United States Patent
Ales

(10) Patent No.: US 10,154,935 B1
(45) Date of Patent: Dec. 18, 2018

(54) PRESSURE BEARING AURICULAR HEMATOMA APPLIANCE

(71) Applicant: Bryan L. Ales, Long Beach, CA (US)

(72) Inventor: Bryan L. Ales, Long Beach, CA (US)

( * ) Notice: Subject to any disclaimer, the term of this patent is extended or adjusted under 35 U.S.C. 154(b) by 84 days.

(21) Appl. No.: 14/120,490

(22) Filed: May 27, 2014

(51) Int. Cl.
| | | |
|---|---|---|
| *A61F 5/08* | (2006.01) | |
| *A61H 1/00* | (2006.01) | |
| A61N 2/00 | (2006.01) | |
| A61B 5/04 | (2006.01) | |
| A61B 5/01 | (2006.01) | |
| A61B 17/11 | (2006.01) | |
| A61B 5/05 | (2006.01) | |
| A61N 2/12 | (2006.01) | |
| A61B 17/10 | (2006.01) | |
| A61N 2/02 | (2006.01) | |
| A61B 17/52 | (2006.01) | |

(52) U.S. Cl.
CPC ............... *A61H 1/008* (2013.01); *A61B 5/01* (2013.01); *A61B 5/04* (2013.01); *A61B 5/05* (2013.01); *A61B 17/10* (2013.01); *A61B 17/11* (2013.01); *A61B 17/52* (2013.01); *A61N 2/00* (2013.01); *A61N 2/004* (2013.01); *A61N 2/02* (2013.01); *A61N 2/12* (2013.01)

(58) Field of Classification Search
CPC .. A61F 5/01; A61F 5/0102; A61F 5/04; A61F 5/048; A61F 5/05; A61F 5/058; A61F 5/05891; A61F 5/24; A61F 5/30; A61F 2005/0172; A61F 2013/00919; A61F 2013/00923; A41D 20/00; A61B 17/10; A61B 17/11; A61B 17/52; A61B 2017/1103; A61B 2017/1107; A61B 2017/1121; A61B 2017/1132; A61B 2017/1139; A61N 2/00; A61N 2/002; A61N 2/004; A61N 2/006; A61N 2/008; A61N 2/02; A61N 2/06; A61N 2/12
See application file for complete search history.

(56) References Cited

U.S. PATENT DOCUMENTS 3,034,320 A   5/1962   Feibelman
3,111,736 A   11/1963  Budreck
(Continued)

FOREIGN PATENT DOCUMENTS

| DE | WO 2012168449 A1 * | 12/2012 | ............. A61F 13/02 |
| GB | WO 2004043539 A1 * | 5/2004 | ............... A61N 2/06 |
| IT | WO 2006048898 A1 * | 5/2006 | ............. A61H 39/04 |

OTHER PUBLICATIONS

The Free Dictionary, Plastic, Apr. 1, 2016, Houghton Mifflin Harcourt Publishing, http://www.thefreedictionary.com/plastic.*

*Primary Examiner* — Alexander Orkin
(74) *Attorney, Agent, or Firm* — Patent Law & Venture Gp.; Gene Scott

(57) ABSTRACT

A pressure bearing appliance for treating an auricular hematoma is taught which incorporates an anterior magnetic disc having a protected permanent magnet, enclosed with an outer soft covering and antimicrobial outside veneer layer placed on a human auricle anterior directly over a hematoma. A posterior magnetic disc protected permanent magnet, enclosed with an outer soft covering and an antimicrobial outside veneer layer is centered on a posterior side of an auricle. Magnetic attraction applies compression therebetween eliminating potential separation between the auricle perichondrium and cartilage during healing.

1 Claim, 2 Drawing Sheets

(56) References Cited

U.S. PATENT DOCUMENTS

| | | | |
|---|---|---|---|
| 5,050,276 A | 9/1991 | Pemerton | |
| 5,690,656 A * | 11/1997 | Cope | A61B 17/11 |
| | | | 128/898 |
| 5,745,921 A * | 5/1998 | Mitchell | A41D 20/00 |
| | | | 2/171 |
| 5,827,212 A * | 10/1998 | Gaskill | A61F 5/058 |
| | | | 91 128/864 |
| 6,305,192 B1 | 10/2001 | Indiveri et al. | |
| 7,793,518 B1 | 9/2010 | Holleman | |
| 8,118,821 B2 * | 2/2012 | Mouw | A61B 17/1114 |
| | | | 606/153 |
| 8,623,036 B2 * | 1/2014 | Harrison | A61B 17/11 |
| | | | 606/153 |
| 8,864,781 B2 * | 10/2014 | Surti | A61B 17/1114 |
| | | | 606/153 |
| 2002/0169357 A1 | 11/2002 | Chen | |
| 2002/0183583 A1 * | 12/2002 | Price | A61N 2/06 |
| | | | 600/15 |
| 2002/0198433 A1 * | 12/2002 | Roberts | A61N 2/008 |
| | | | 600/9 |
| 2007/0270631 A1 * | 11/2007 | Nelson | A61F 2/00 |
| | | | 600/12 |
| 2008/0051621 A1 * | 2/2008 | Vines | A61N 2/06 |
| | | | 600/15 |
| 2008/0086067 A1 | 4/2008 | Hay et al. | |
| 2009/0062825 A1 * | 3/2009 | Pool | A61F 5/003 |
| | | | 606/157 |
| 2009/0130157 A1 * | 5/2009 | Ylitalo | A01N 25/34 |
| | | | 424/405 |
| 2009/0182255 A1 | 7/2009 | Hay et al. | |
| 2010/0069813 A1 * | 3/2010 | Crisp | A61F 13/00008 |
| | | | 602/46 |
| 2012/0197062 A1 * | 8/2012 | Requarth | A61B 17/11 |
| | | | 600/12 |
| 2015/0173852 A1 * | 6/2015 | Khakpour | A61C 5/02 |
| | | | 433/27 |
| 2015/0200046 A1 * | 7/2015 | Park | G01R 33/3873 |
| | | | 335/302 |

* cited by examiner

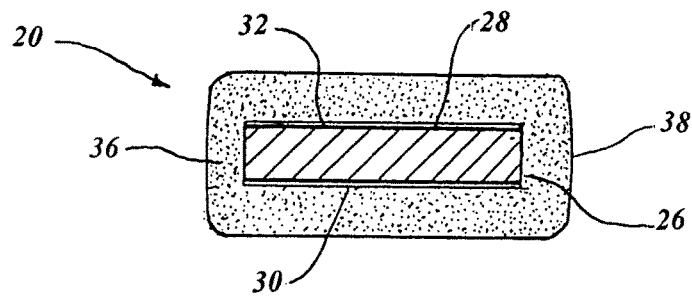
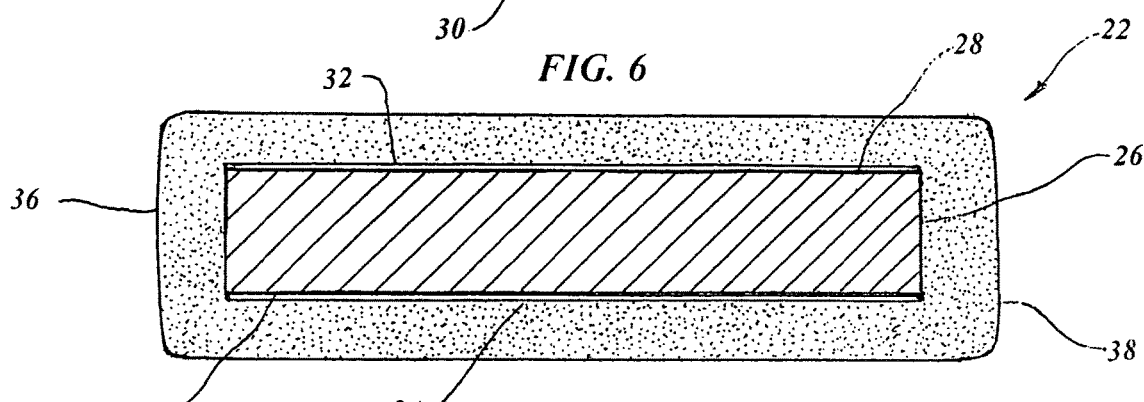
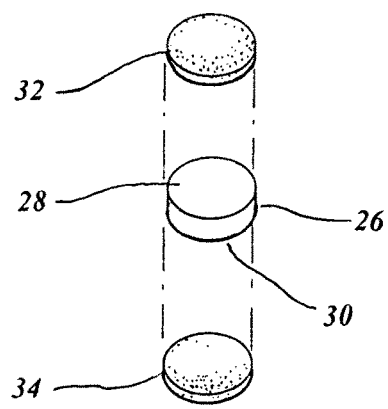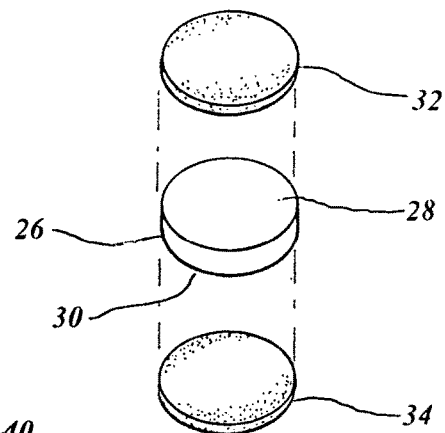
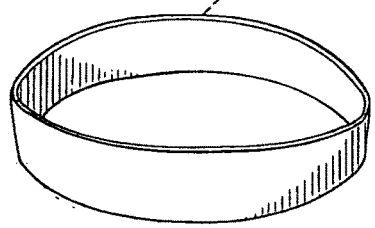

PRESSURE BEARING AURICULAR HEMATOMA APPLIANCE

TECHNICAL FIELD

The present invention relates to medical appliances for outer ears in general. More specifically to a pressure bearing device used for compression of the skin/tissue of a human ear for therapeutic treatment of auricular hematomas.

BACKGROUND ART

Previously, many types of magnetic assemblies have been used in endeavoring to provide an effective means to utilize magnetic attraction to connect items together or to apply an attractive force through material or human tissue.

The prior art listed below did not disclose patents that possess any of the novelty of the instant invention: however the following U.S. patents are considered related:

| Pat. No. | Inventor | Issue Date |
|---|---|---|
| 3,034,320 | Feibelman | May 15, 1962 |
| 3,111,736 | Budreck | Nov. 26, 1963 |
| 5,050,276 | Pemerton | Sep. 24, 1991 |
| 6,305,192 | Indiveri et al. | Oct. 23, 2001 |
| 7,793,518 B1 | Holleman | Sep. 14, 2010 |
| patent application Publication No. | | |
| US2002/0169357 A1 | Chen | Nov. 14, 2002 |
| WO2004078028 A1 | Avicola et al. | Sep. 16, 2004 |
| U52008/0086067 A1 | Hay et al. | Apr. 10, 2008 |
| US 2009/0182255 A1 | Hay et al. | Jul. 16, 2009 |

Feibelman in U.S. Pat. No. 3,034,320 teaches the incorporation of magnetic elements, one of which has an earring ornament secured thereto and is positioned on the front side of the wearer's ear. The other element, which is independent of the first magnet element, is positioned on the ear side of the wearer's ear. The magnetic elements are effective in retained the device on the wearers ear by their magnetic attraction.

U.S. Pat. No. 5,050,276 issued to Pemerton is for a magnetic clasp having two mirror image halves each of which are attach to the ends of a necklace. Each half has a magnetic shell and an inserted magnetic core. The shell has a cylindrical body with a cone-shaped end. The front of the shell has an open cavity for inserting a magnetic core.

Budreck in U.S. Pat. No. 3,111,736 teaches a two part magnetic connector primarily used for automotive keys. The owner retains the magnetic part leaving the armature part with an attendant. Two counterpart magnet assemblies, each include a permanent magnet and a pole cup. The magnet nests within the rim of the cup which is spaced from the magnet body to create a dielectric gap in the magnetic flux. Each assembly has a different magnitude thus creating a self centering feature.

Holleman in U.S. Pat. No. 7,793,518 B1 discloses a clasp consisting of an outside member and an internal surface having a decorated external surface also an internal surface containing an imbedded first magnet. The inside member contains a second magnet imbedded in its internal surface. The clasp functions by placing the outside member on an outer surface of a garment them gathering the material with a chain while placing the inside member opposite the outside member on an inner surface of a clothing garment.

Patent Application Publication No. US2008/0086067 A1 issued to Hay et al. is for a non-evasive ear compression dressing or splinting device for prevention, treatment and recurrence of injuries to the outer ear such as auricular hematoma. The device includes a structure including a pair of first and second pads, and a pressure applying assembly. The pads are assembled in pairs in opposing facing relation to compressibly engage the injured portion of an external ear.

Hay et al. in Patent Application Publication No. US 2009/0182255 A1 discloses an improved non-evasive ear compression dressing or splinting device for prevention, treatment and recurrence of injuries to the outer ear such as auricular hematoma. The device includes a structure including a pair of first and second pads, and a pressure applying assembly. The pads are assembled in pairs in opposing facing relation to compressibly engage the injured portion of an external ear. The pressure applying assembly includes an adjustment mechanism for forcing one pad assembly towards the other in continuously adjustable controlled manner creating a compression of the ear tissue required for healing between the two opposing pads.

For background purposes and as indicative of the art to which the invention is related reference may be made to the remaining cited patent and patent application publication numbers U.S. Pat. No. 6,305,192, US2002/0169357 A1 and WO2004078028 A1.

DISCLOSURE OF THE INVENTION

A human outer ear, which is actually designated as the auricle, may be easily damaged particularly in contact sports where the auricle is basically unprotected or in association with some blow or a hard surface. The auricle is skin covered cartilage with only a thin padding of connective tissue, therefore even rough handling may cause swelling sufficient enough to endanger the blood supply available within the connective tissue which provides nourishment for the cartilage. The cartilage structure is fed by a thin covering perichondrium membrane and therefore any fluid or blood from the swelling may collect between the perichondrium and the underlying cartilage which creates a separation of the required nutrients provided in the blood. When this separation takes place the cartilage dies and will not heal back into its normal shape, instead it becomes lumpy and distorted which is commonly called a cauliflower ear.

There has been a long felt need to provide some means to prevent the formation of a distorted cartilage in a comfortable manner therefore it is the primary object of the invention to utilize an appliance that provides constant pressure on the hematoma during the normal healing process.

An important object of the invention is the use of two magnets, one on each exposed side of the auricle with the combination creating sufficient magnetic attraction between opposed magnets to provide the constant pressure required. The hematoma must be drained before applying the appliance to permit nourishment to reach the cartilage.

Another object of the invention is that it is soft enough to essentially comply with the contour of the specific auricle. This feature is accomplished by the inclusion of an outer covering which is both soft and spongy and yet not unnecessarily thick so as to be unwieldy and yet still providing the necessary magnetic attraction.

Still another object of the invention is the outer covering creates a hermetic seal to isolate the magnet from contact with the auricle. This outer covering is made of a malleable, pliable and soft material preferably of silicone.

A further object is the incorporation of an antimicrobial outside veneer layer which is an agent that kills microorganisms and/or inhibits microorganism growth. This medication is particularly useful as the hematoma requires draining during treatment leaving a small puncture opening that could be subject to an infection or disease.

Yet another object of the invention is in the use of safety protecting guards on both sides of each disc which allows adequate strength for retaining the integrity of permanent magnet in the event of inadvertent breakage which completely prevents sharp edges from being in contact with the wearer's ear.

A further aspect of the invention is that either side of the disc may be applied to the auricle thus eliminating specific directive indicia to be necessary when attaching the appliance.

A final object of the invention is directed to the size of the anterior disc and posterior disc which may be selected according to the position of the hematoma and the configuration as well as the thickness of the auricle. It is anticipated that sets of sizes and strengths may be utilized by the provider or user when initially fitting the appliance, These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 6 is an enlarged cross sectional view taken along an arbitrary center line of the anterior magnetic disc of FIG. 4.

FIG. 7 is an enlarged cross sectional view taken along an arbitrary center line of the posterior magnetic disc of FIG. 5.

FIG. 8 is an exploded view of the anterior magnetic disc and the safety protective guards, however less the outer covering.

FIG. 9 is an exploded view of the posterior magnetic disc and the safety protective guards, however less the outer covering.

FIG. 10 is a partial isometric view of the night headband.

BEST MODE FOR CARRYING OUT THE INVENTION

Figures 1, 2, 3, 4, 5:
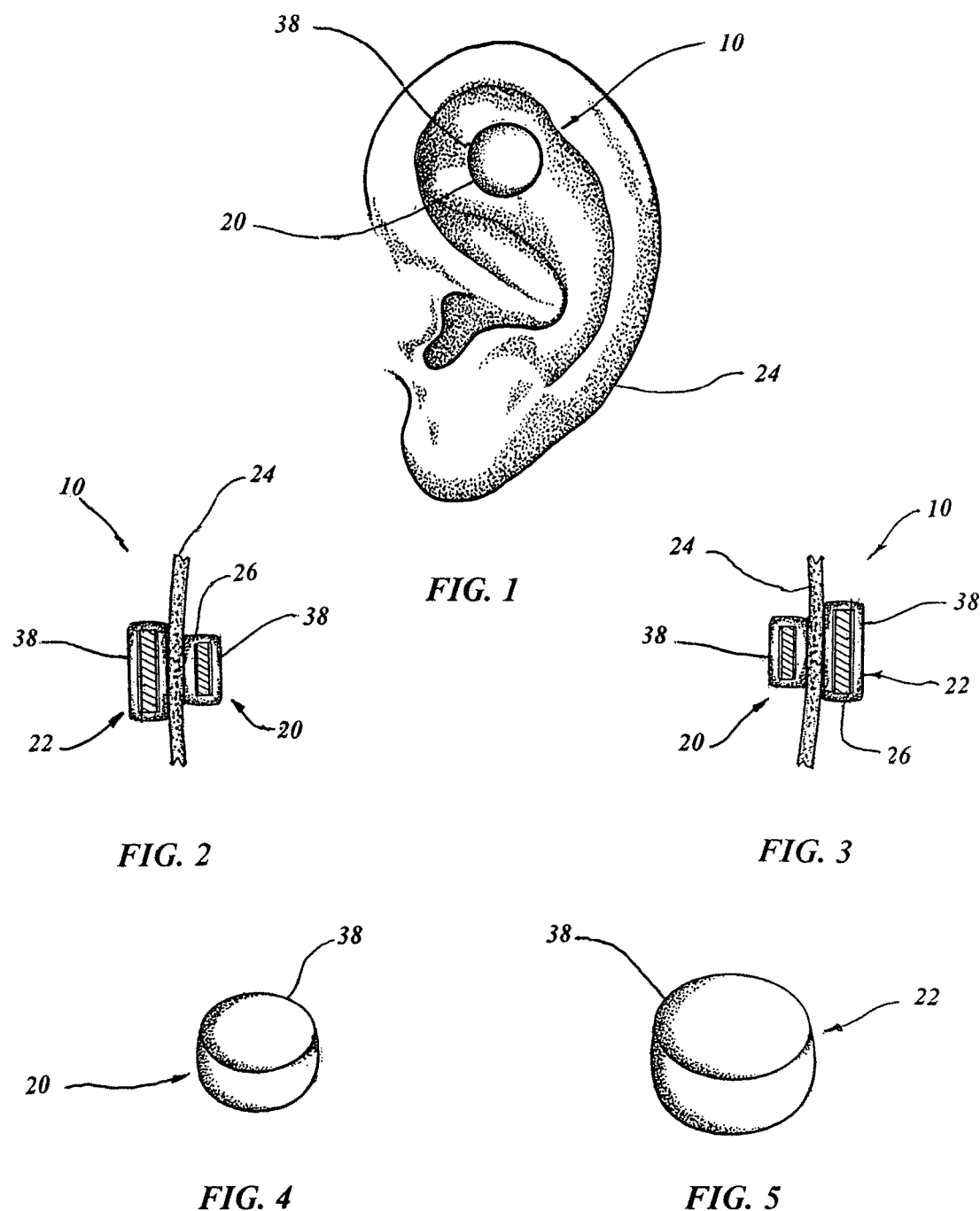
FIG. 1 is an orthographic view a typical human auricle with the anterior hematoma appliance in place.
FIG. 2 is a partial cross sectional view taken along an arbitrary center line of FIG. 1.
FIG. 3 is a partial cross sectional view taken along an arbitrary line of FIG. 1 except from an opposed side of FIG. 2.
FIG. 4 is a partial isometric view of the anterior magnetic disc in the preferred embodiment.
FIG. 5 is a partial isometric view of the posterior magnet disc in the preferred embodiment.

The best mode for carrying out the invention is presented in terms of a preferred embodiment. This preferred embodiment is shown in FIGS. 1 thorough 10 and is comprised of a pressure bearing appliance 10 for treating an auricular hematoma consisting of two devices used jointly, an anterior magnetic disc 20 and a posterior magnet disc 22. When the anterior magnetic disc 20 is placed on the anterior side of a human auricle 24 directly over a drained hematoma, and the posterior magnetic disc 22 is centered on the posterior side of the auricle 24, the magnetic attraction applies compression therebetween impeding separation between the auricle 24 perichondrium and cartilage. The physical size of the anterior disc 20 and posterior disc 22 is preferably selected according to the position of the hematoma, the configuration, and the thickness of the auricle. It is therefore required that sets of sizes and strengths are utilized by the provider, or by the user, when initially fitting the appliance.

In an embodiment, an encapsulated magnetic assembly 20 (or 22) is used for compressive contact with ear surfaces as shown by either FIG. 4 or FIG. 5. The assembly 20 comprises a flat circular permanent magnet 26, and a pair of flat circular metal plates 32 and 34 capable of resisting penetration by magnet splinters. The magnet 26 is positioned between metal plates 32, 34 and magnet 26 and metal plates 32, 34 have mutually aligned peripheral edges as shown in FIGS. 6 and 7. The magnet 26 and metal plates 32, 34 are fully encapsulated within a malleable, pliable, and soft silicone material 36 which is positioned as an outer layer around assembly 20. Silicone material 36 has a top portion in contact with a first one of said metal plates 32, a bottom portion in contact with a second one of said metal plates 34 and a peripheral portion in contact with said aligned peripheral edges as shown. In accordance with common usage, "malleable" herein means: capable of deformation without breaking, when subject to compressive stress; "pliable" herein means: easily bent, flexible, supple; and "soft" herein means yielding readily to pressure so as to change shape.

The anterior magnetic disc 22 contains a circular, flat permanent magnet 26, having a front flat side 28 and a rear flat side 30, shown best in FIGS. 6-9. The permanent magnet 26 has a magnetic strength value of N35 to N52 or a rating of at least 20,000 gausses. It will be noted however that gauss strength may be misleading as the strength of the magnetic field falls off very quickly as the distance between magnets and the thickness and substance of the auricle 24 must be accounted for. Actual gauss strength within human tissue can be much less than the gauss rating of the magnet as the material and substance of the magnet alone does not determine the ultimate strength however it has been found through analytical testing that the gauss rating of 20,000 is more than sufficient to accomplish the pressure bearing requirement. For an example a neodymium magnet of a ½ inch diameter and ⅛ inch thickness is rated at 12,000 gausses which is about the minimum practical diameter to fit within a human outer ear and it is entirely adequate for the application.

The permanent magnet 26 incorporates a material consisting of a rare earth neodymium-iron-boron, a rare earth neodymium-iron-boron bonded with epoxy resin, a samarium cobalt grade 2-7, a samarium cobalt grade 1-5, an aluminum-nickel-cobalt grade 5 or an aluminum-nickel-cobalt grade 8. It has been found the preeminent size of the permanent magnet 26 has a minimum diameter of 0.25 inch (6.35 mm) to a maximum diameter of 1.00 inch (25.41 mm) and a nominal thickness of from 0.0625 inch (1.59 mm) to 0.250 inch (6.35 mm). The permanent magnet 26 is the disc type either the plain disc type magnet or a nickel plated disc type.

A front safety protecting guard 32 is adhered to the permanent magnet front flat side 28 and a rear safety protecting guard 34 adhered to said permanent magnet rear flat side 30 each having adequate strength to retain the integrity of the permanent magnet 26 in the event of inadvertent breakage which would prevent any sharp edges to be in contact with a wearer of the pressure bearing appliance 10.

The front and rear safety protecting guard 32 and 34 base material may be any base substance having a thickness of from 0.002 inch (0.051 mm) to 0.125 inch (3.18 mm) such as paper, vinyl, cardboard, cloth, rubber, thermoplastic, felt, nylon or metal. The front and rear safety protecting guard 32 and 34 are adhered to the permanent magnet 26 with a bonding agent such as pressure sensitive tape, glue, rubber cement, epoxy resin, cyanoacrylate, polyester resin and polyurethane resin, with pressure sensitive tape preferred.

An outer covering 36 completely encloses the permanent magnet 26 in concert with the front and rear safety protecting guard 32 and 34 and has a thickness have a thickness of from 0.031 inches (0.80 mm) to 0.250 inches (6.35 mm). The outer covering 36 is hermetically sealed and completely water tight and is preferably comprised of a silicone sealant material, however other suitable materials may include synthetic rubber, poly vinyl chloride (PVC) or ethylene propylene diene monomer (EPDM) with equal ease. While any color is acceptable in the application, however skin shade is preferred.

An antimicrobial outside veneer layer 38 applied over said outer covering which is any agent that kills microorganisms or inhibits their growth however silver sulfadiazine and its derivatives is preferred. This medication is particularly useful as the hematoma requires draining leaving a small puncture opening that could be subject to an infection or disease.

The posterior magnet disc 22 is basically the same as the anterior magnet disc 24 with the exception of its size wherein the anterior magnetic disc 22 is smaller in diameter and thickness than said posterior magnetic disc 24 creating a self centering relationship therebetween. The size difference is shown clearly in FIGS. 2 through 9. As the internal elements are exactly the same in the drawings and above descriptions. In order to avoid unnecessary repetition the same element designation is used for both magnetic discs 22 and 24 regardless of their size differential.

A night headband 40, as illustrated in FIG. 10, may be utilized for covering a wearers head during pressure bearing appliance treatment for an auricular hematoma.

The night headband 40 may be any configuration with a width of from 2 inches (5.80 cm) to 4 inches (10.16 cm) and a circumference of from 12 inches (30.48 cm) to 20 inches (50.80 cm) with the material consisting of cotton, stretch weave, elastic blended cotton, microfiber or the like.

While the invention has been described in complete detail and pictorially shown in the accompanying drawings, it is not to be limited to such details, since many changes and modifications may be made to the invention without departing from the spirit and scope thereof. Hence, it is described to cover any and all modifications and forms which may come within the language and scope of the appended claims.

The invention claimed is:

1. A pressure bearing appliance for treating an auricular hematoma, said pressure bearing appliance including an anterior magnet assembly for being positioned against an anterior side of said auricular hematoma, and a posterior magnet assembly for being positioned against a posterior side of said auricular hematoma, whereby magnetic attraction between said magnet assemblies applies compression to said auricular hematoma thereby impeding separation between an auricle perichondrium and an opposing cartilage, wherein each one of said magnet assemblies comprises:

a flat circular permanent magnet having a diameter of between 0.25 inch and 1.00 inch, and a thickness of between 0.0625 inch and 0.25 inch;

a pair of flat circular metal plates, each having a thickness of approximately 0.125 inch, and capable of resisting penetration by magnet splinters;

wherein said flat circular permanent magnet is positioned between said flat circular metal plates and bonded thereto by one of epoxy resin, polyester resin, and polyurethane resins;

wherein said flat circular permanent magnet and said flat circular metal plates have mutually aligned peripheral edges;

wherein said flat circular permanent magnet and said flat circular metal plates are fully encapsulated within a silicone material having a thickness of between 0.031 and 0.250 inches; and wherein said silicone material is coated with an antimicrobial veneer layer of silver sulfadiazine.

* * * * *